(12) United States Patent
Verzal et al.

(10) Patent No.: US 8,249,720 B2
(45) Date of Patent: Aug. 21, 2012

(54) COMPRESSION MEMBER SUTURE SLEEVE (75) Inventors: Kevin E. Verzal, Minneapolis, MN (US); Adam J. Rivard, Blaine, MN (US); Mohan Krishnan, Shoreview, MN (US); G. Shantanu Reddy, Minneapolis, MN (US); Patsy A. Coppola, Bedford, MA (US); Edward L. Dickinson, Littleton, MA (US); Andrew C. Harvey, Waltham, MA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 238 days.

(21) Appl. No.: 12/265,282

(22) Filed: Nov. 5, 2008

(65) Prior Publication Data

US 2009/0125059 A1    May 14, 2009

Related U.S. Application Data

(60) Provisional application No. 60/986,915, filed on Nov. 9, 2007, provisional application No. 60/986,922, filed on Nov. 9, 2007, provisional application No. 60/986,911, filed on Nov. 9, 2007.

(51) Int. Cl.
*A61N 1/05* (2006.01)
(52) U.S. Cl. .................. 607/116; 606/232; 607/126
(58) Field of Classification Search .................. 607/116, 607/126; 606/232; 29/557
See application file for complete search history.

(56) References Cited

U.S. PATENT DOCUMENTS

| | | | |
|---|---|---|---|
| 4,266,552 A | 5/1981 | Dutcher et al. | |
| 4,276,882 A | 7/1981 | Dickhudt et al. | |
| 4,287,891 A | 9/1981 | Peters | |
| 4,387,727 A | 6/1983 | Sandstrom | |
| 4,437,475 A | 3/1984 | White | |
| 4,516,584 A | 5/1985 | Garcia | |
| 4,538,623 A | 9/1985 | Proctor et al. | |
| 4,553,961 A | 11/1985 | Pohndorf et al. | |
| 4,613,329 A | 9/1986 | Bodicky | |
| 4,615,472 A | 10/1986 | Nash | |
| 4,672,979 A | 6/1987 | Pohndorf | |
| 4,676,782 A | 6/1987 | Yamamoto et al. | |
| 4,683,895 A | 8/1987 | Pohndorf | |
| 4,768,523 A | 9/1988 | Cahalan et al. | |

(Continued)

OTHER PUBLICATIONS

"Suture Sleeve with Removable Fins", Technical Disclosure from www.ip.com, No. IPCOM000125732D, published Jun. 15, 2005, full document available at http://www.ip.com/pubview/IPCOM000125732D, 4 pages.

(Continued)

*Primary Examiner* — George Manuel
*Assistant Examiner* — Alyssa M Alter
(74) *Attorney, Agent, or Firm* — Faegre Baker Daniels LLP (57) ABSTRACT

An implantable medical system includes a medical lead including an insulating sheath and a conductor and an anchoring device. The anchoring device defines an inner lumen adapted to coaxially receive the medical lead, where the inner lumen has an effective diameter. The anchoring device includes a sleeve including a substantially elongate body defining an outer surface and an inner bore. The anchoring device also has a compression member including a first end, a second end, and an intermediate portion between the first and second ends. The compression member is at least partially embedded in the sleeve such that compression of the first and second ends of the compression member toward one another causes the effective diameter of at least a portion of the inner lumen of the anchoring device to reversibly increase.

14 Claims, 5 Drawing Sheets

U.S. PATENT DOCUMENTS

| | | | |
|---|---|---|---|
| 4,906,233 A * | 3/1990 | Moriuchi et al. | 604/174 |
| 5,036,862 A | 8/1991 | Pohndorf | |
| 5,107,856 A | 4/1992 | Kristiansen et al. | |
| 5,129,405 A | 7/1992 | Milijasevic et al. | |
| 5,152,298 A | 10/1992 | Kreyenhagen et al. | |
| 5,242,431 A | 9/1993 | Kristiansen | |
| 5,257,975 A | 11/1993 | Foshee | |
| 5,273,053 A | 12/1993 | Pohndorf | |
| 5,376,108 A | 12/1994 | Collins et al. | |
| 5,423,763 A | 6/1995 | Helland et al. | |
| 5,476,493 A * | 12/1995 | Muff | 607/119 |
| 5,549,619 A | 8/1996 | Peters et al. | |
| 5,583,319 A * | 12/1996 | Lieurance | 174/84 R |
| 5,584,874 A | 12/1996 | Rugland et al. | |
| 5,603,730 A | 2/1997 | Romkee | |
| 5,628,780 A | 5/1997 | Helland et al. | |
| 5,674,273 A | 10/1997 | Helland | |
| 5,683,403 A | 11/1997 | Adams et al. | |
| 5,683,446 A | 11/1997 | Gates | |
| 5,709,644 A | 1/1998 | Bush | |
| 5,735,891 A | 4/1998 | White | |
| 5,746,722 A | 5/1998 | Pohndorf et al. | |
| 5,824,032 A | 10/1998 | Belden | |
| 5,827,296 A | 10/1998 | Morris et al. | |
| 5,843,146 A | 12/1998 | Cross, Jr. | |
| 5,876,429 A | 3/1999 | Schroeppel | |
| 5,957,968 A | 9/1999 | Belden et al. | |
| 6,002,969 A | 12/1999 | Machek et al. | |
| 6,259,953 B1 | 7/2001 | Lucchesi et al. | |
| 6,473,654 B1 | 10/2002 | Chinn | |
| 6,554,802 B1 | 4/2003 | Pearson et al. | |
| 6,592,553 B2 | 7/2003 | Zhang et al. | |
| 6,901,287 B2 | 5/2005 | Davis et al. | |
| 6,921,295 B2 * | 7/2005 | Sommer et al. | 439/668 |
| 6,985,777 B2 | 1/2006 | Tsuboi et al. | |
| 7,082,337 B2 | 7/2006 | Sommer et al. | |
| 7,184,841 B1 | 2/2007 | Bodner et al. | |
| 7,218,972 B2 | 5/2007 | Rodriguez | |
| 7,242,986 B2 | 7/2007 | Rodriguez | |
| 7,248,930 B1 | 7/2007 | Woloszko et al. | |
| 7,398,125 B2 * | 7/2008 | Osypka et al. | 607/119 |
| 2003/0050668 A1 | 3/2003 | Lee | |
| 2003/0195600 A1 | 10/2003 | Tronnes et al. | |
| 2003/0220678 A1 | 11/2003 | Tronnes et al. | |
| 2004/0059403 A1 | 3/2004 | Massullo | |
| 2004/0254623 A1 | 12/2004 | Rodriguez et al. | |
| 2005/0080470 A1 | 4/2005 | Westlund et al. | |
| 2005/0177220 A1 | 8/2005 | Iaizzo et al. | |
| 2006/0235484 A1 | 10/2006 | Jaax et al. | |
| 2006/0264803 A1 | 11/2006 | Lui et al. | |
| 2007/0078399 A1 | 4/2007 | Olson | |
| 2009/0125058 A1 | 5/2009 | Bodner et al. | |
| 2009/0125060 A1 | 5/2009 | Rivard et al. | |
| 2009/0125061 A1 | 5/2009 | Rivard et al. | |

OTHER PUBLICATIONS

"Pacing Lead Stabilizer with Modified Slit Geometry", Technical Disclosure from www.ip.com, No. IPCOM000130753D, published Nov. 3, 2005, full document available at http://www.ip.com/pubview/IPCOM000130753D, 6 pages.

* cited by examiner

COMPRESSION MEMBER SUTURE SLEEVE

CROSS REFERENCE TO RELATED APPLICATIONS

This application claims priority under 35 U.S.C. §119(e) to U.S. Provisional Patent Application No. 60/986,915, filed on Nov. 9, 2007, entitled "COMPRESSION MEMBER SUTURE SLEEVE," U.S. Provisional Patent Application No. 60/986,922, filed on Nov. 9, 2007, entitled "PRE-SELECTED COMPRESSION LEAD ANCHORING DEVICE," and U.S. Provisional Patent Application No. 60/986,911, filed on Nov. 9, 2007, entitled "COMPRESSION CONTROL LEAD ANCHORING DEVICE," all of which are incorporated herein by reference in their entirety.

TECHNICAL FIELD

The present invention relates generally to suture sleeves for anchoring medical leads to tissue of a patient. More specifically, the present invention relates to suture sleeves having compression control features.

BACKGROUND

Medical leads are anchored to a patient's tissue in a variety of applications using anchoring devices, including those commonly referred to as "suture sleeves." For example, in many left ventricular pacing applications, an electrical lead connected to a cardiac rhythm management (CRM) device, such as a pacemaker, is secured to patient tissue at a vein entry site to help prevent both acute and chronic lead migration and dislodgement. In particular, leads are secured in place by securing a suture sleeve about the insulation of the lead and suturing the suture sleeve to the patient's tissue.

SUMMARY

Various embodiments of the medical system and anchoring device are characterized by one or more of applying a predetermined retaining force on a lead, applying a predetermined retaining force on a lead which has a magnitude independent of a user input, such as tying force, limiting a maximum compressive force to be applied to a lead, providing tactile feed back that such a limit has been reached, serving to distribute otherwise concentrated crushing forces across a broader lead area, accommodating sliding along the length of the lead prior to suture tie down when the anchoring device is in an open state; and allowing sufficient compressive force to be exerted on leads to stabilize them axially after tie down, as well as other additional or alternate desirable features.

One aspect of the invention relates to implantable medical systems. In some embodiments, an implantable medical system includes a medical lead including an insulating sheath and a conductor and an anchoring device. The anchoring device defines an inner lumen adapted to coaxially receive the medical lead, where the inner lumen has an effective diameter. The anchoring device includes a sleeve including a substantially elongate body defining an outer surface and an inner bore. The anchoring device also has a compression member including a first end, a second end, and an intermediate portion between the first and second ends. The compression member is at least partially embedded in the sleeve such that compression of the first and second ends of the compression member toward one another causes the effective diameter of at least a portion of the inner lumen of the anchoring device to reversibly increase.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
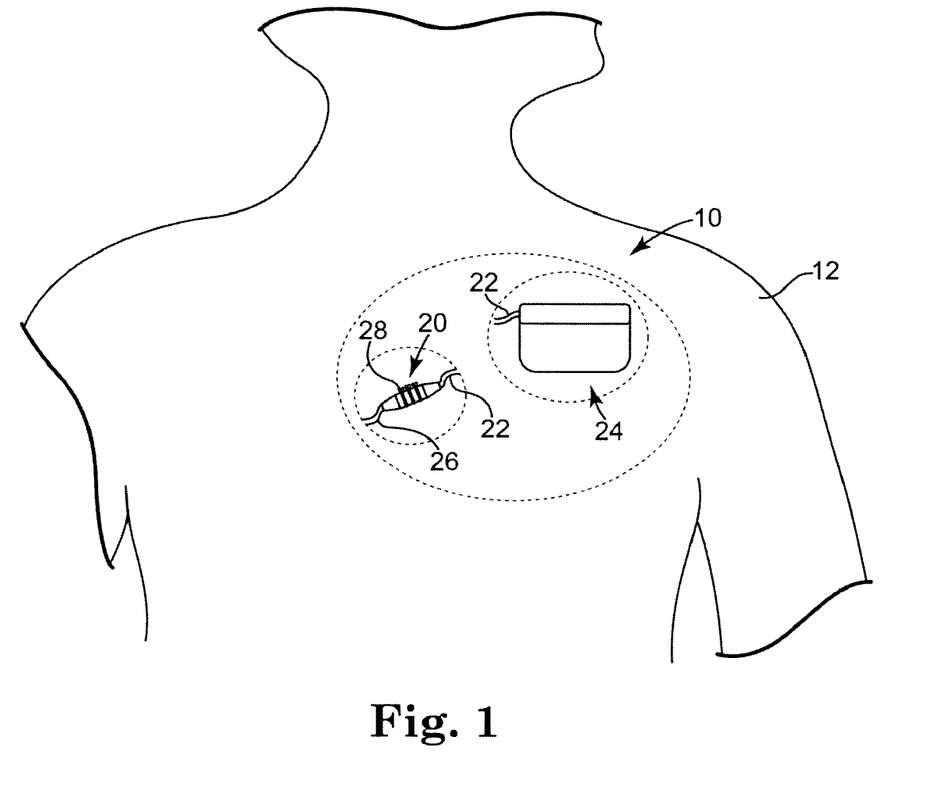
FIG. 1 is a simplified view of an anchoring system implanted in a patient's body (designated generally by a circle in FIG. 1), according to various embodiments of the invention.

FIG. 1 is a simplified view of a medical system 10 implanted in a patient's body 12 according to various embodiments of the invention. The system 10 includes an anchoring device 20 (also described as a suture sleeve 20), a lead 22, and an implanted medical device (IMD) 24 connected to the lead 22. In some embodiments, the IMD 24 is a cardiac rhythm management (CRM) device (e.g., a pacemaker or defibrillator) or other therapeutic device (e.g., a drug pump) implanted in the body 12.

In some embodiments, the lead 22 is an electrical lead of a type suitable for use with CRM devices, for example. The lead 22 includes one or more inner conductors (not shown) or other internal features and an outer, insulating sheath 26 extending over the internal features of the lead 22. In some embodiments, the lead 22 includes electrodes (not shown) or other features for stimulating or sensing functionality. The lead 22 is generally characterized by a maximum radial crushing force, or maximum compressive force, that the lead 22 can withstand prior to sustaining damage.

As shown in FIG. 1, and in general terms, the anchoring device 20 is positioned over the insulating sheath 26 of the lead 22 and serves to stabilize the lead 22 at or near a vein entry site (not shown) to help prevent both acute and chronic lead migration and dislodgement. In some embodiments, the anchoring device 20 is compressed onto the lead 22 using sutures 28 secured about the anchoring device 20. According to some methods, the sutures 28 are manually secured about the anchoring device 20 by a physician using some tension or tying force. The tying force often varies from about 1 to about 8 pounds or more.

Although the sutures 28 are optionally used to compress the anchoring device 20 onto the lead 22 for lead retention, in other embodiments, the anchoring device 20 is sufficiently "self-retaining" on the lead 22 that the compressive forces from the sutures 28 are not necessary to sufficiently secure the anchoring device 20 to the lead 22 for long term implantation (though the sutures 28 may still be present to secure the anchoring device 20 to adjacent tissue of the patient's body 12). Additionally, although sutures in general, and manual methods of tying of sutures 28 in particular are referenced herein, other fastening means and methods, such as spring clips or automatic suture tying devices, use of a tool to gain mechanical advantage, for example, are also contemplated.

In general terms, the anchoring device 20 is adapted for improved lead retention that, in some embodiments, has a predetermined magnitude that is substantially consistent and independent of user technique. The anchoring device 20 also optionally acts to minimize deformation or other damage to the insulating sheath 26 and its internal features (e.g., conductive coils). For example, the conductors and/or insulative sheath 26 can be damaged by concentrated radial forces at the interface between the lead 22 and the anchoring device 20 proximate the sutures 28 if insufficiently protected. Deformation of the conductors (e.g., coils) can reduce efficacy or even result in complete failure (e.g., shorting) of the lead 22. The lead 22 can also sustain damage to the insulating sheath 26, for example if the sutures 28 cut through the anchoring device 20 and then into the insulating sheath 26.

Figure 2:
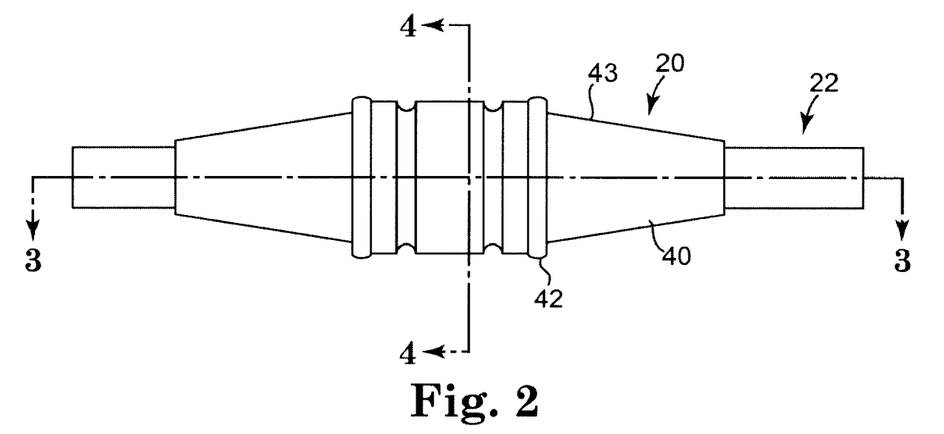
FIG. 2 shows an anchoring device of the anchoring system of FIG. 1, according to some embodiments.

FIG. 2 shows the anchoring device 20 from a front view according to some embodiments. As shown in FIG. 2, the anchoring device 20 includes a sleeve 40 and a compression member 42. The anchoring device 20 also has an outer surface 43 and an inner lumen 44 (see FIG. 3) adapted to receive the lead 22 and is substantially elongate, tubular, and tapers down in diameter toward each end of the anchoring device 20.

Figure 3:
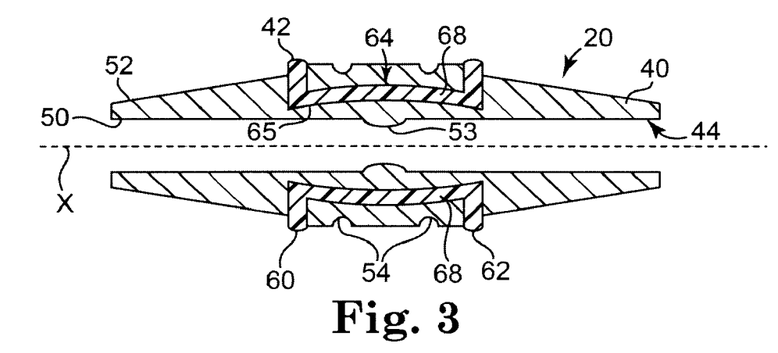
FIG. 3 is a cross-sectional view of the anchoring device of FIG. 2 taken along line 3-3 of FIG. 2.
Figure 4:
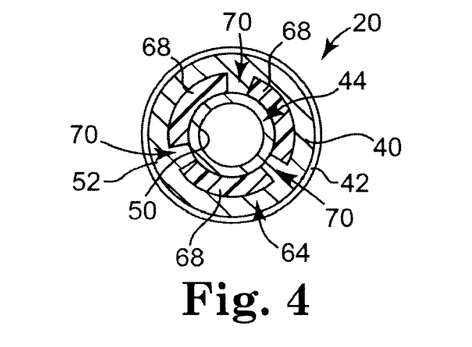
FIG. 4 is a cross-sectional view of the anchoring device of FIG. 2 taken along line 4-4 of FIG. 2.

FIG. 3 is a longitudinal cross-sectional view of the anchoring device 20 taken along line 3-3 of FIG. 2. FIG. 4 is a transverse cross-sectional view of the anchoring device 20 taken along line 4-4 of FIG. 2. As shown in FIGS. 3 and 4, the sleeve 40 generally defines the substantially elongate, hollow, tubular, and tapered shape of the anchoring device 20. The sleeve 40 has a central longitudinal axis X, an inner bore 50, and an outer surface 52. According to some embodiments, the sleeve 40 is formed of an elastomeric material and is generally flexible, substantially compliant, and elastically compressible. For example, the sleeve 40 is formed of silicone or other biocompatible material having suitable properties.

The outer surface 52 has a plurality of circumferentially extending suture grooves 54 formed into the outer surface 52. The sleeve 40 also optionally includes features such as longitudinal slots (not shown) for facilitating compression of the sleeve 40.

The inner bore 50 has a centrally-located and circumferentially-extending raised portion 53 which functions to enhance friction between the lead 22 and the anchoring device 20, although smooth-bored embodiments, as well as additional or alternate roughening or other friction enhancing features are also contemplated.

The inner bore 50 of the sleeve 40 defines an effective diameter along its length. Where a portion of the inner bore 50 is substantially circular in shape, the effective diameter of that portion of the inner bore 50 is essentially the corresponding diameter of the inner bore 50. Where a portion of the inner bore 50 is substantially non-circular in shape (e.g., oval-shaped), the effective diameter of that portion generally corresponds to the largest circle that could be fit through that portion of the inner bore 50 without having to deform that portion of the inner bore 50.

In the case of an oval shape, the effective diameter corresponds to the minor axis of the oval shape. In the case of a square shape, the effective diameter corresponds to the length of one of the sides of the square shape, and so forth. As shown in FIG. 3, the effective diameter of the inner bore 50 is substantially constant up to the raised portion 53, where the effective diameter of the inner bore 50 decreases to a minimum effective diameter of the inner bore 50.

Figure 5:
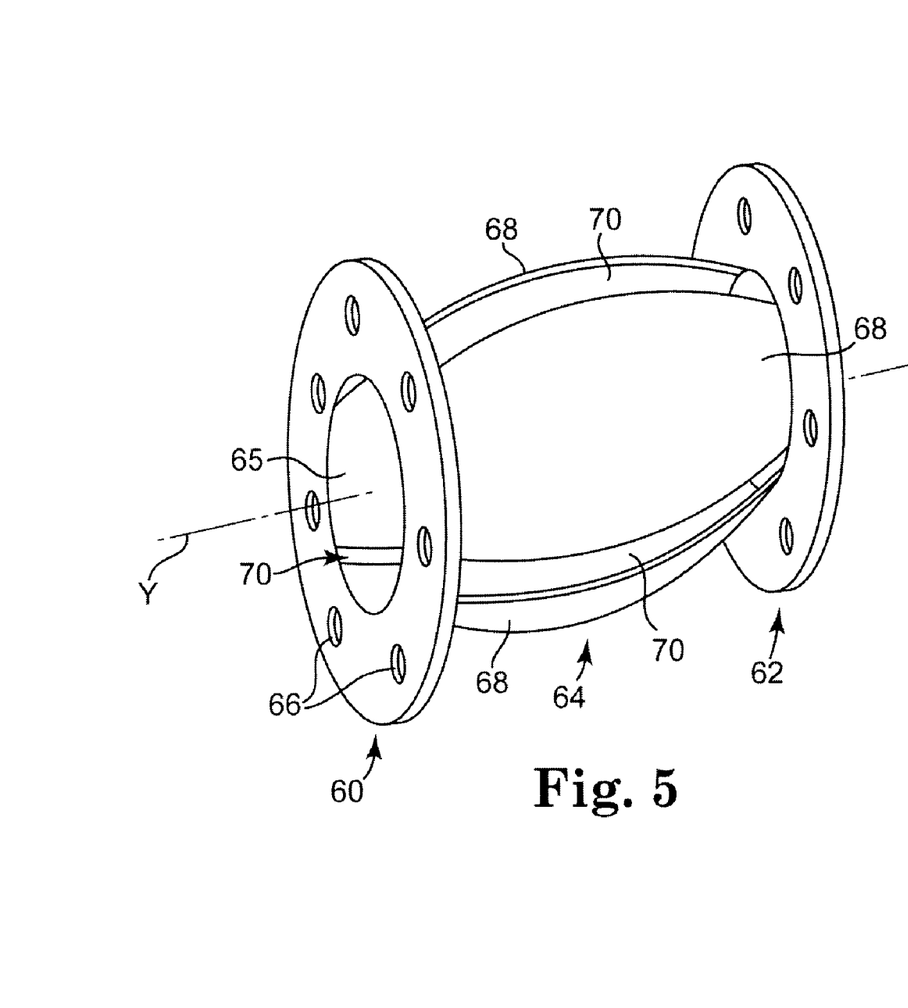
FIG. 5 is an isometric view of a compression member of the anchoring device of FIG. 2.

FIG. 5 is an isometric view of the compression member 42. As shown in FIGS. 3-5, the compression member 42 defines a central longitudinal axis Y and includes a first end portion 60, a second end portion 62 (FIGS. 3 and 5), and an intermediate portion 64 extending between the first and second end portions 60, 62. The compression member 42 also defines an inner lumen 65. Each of the first and second end portions 60, 62 is formed as a substantially annular collar having a plurality of through holes 66 (FIG. 5). The optional through holes 66 help improve interlocking of the compression member and sleeve materials, with portions of the sleeve 40 extending through the holes 66, as subsequently described.

The intermediate portion 64 is formed of a plurality of arcuate bands 68 (e.g., three as shown in FIGS. 3-5). The arcuate bands 68 are disposed radially about a central longitudinal axis Y with gaps 70 between adjacent bands 68. As shown, the bands 68 are curved in a transverse plane of the compression member 42 (FIG. 4) and are also curved along their lengths (FIG. 3) such that they are each substantially cupped in shape, or cup-shaped.

The bands 68 are adapted to elastically deform outwardly away from one another relative to the central longitudinal axis Y upon compression of the first and second end portions 60, 62 toward one another along the central longitudinal axis Y. In particular, as the two end portions 60, 62 are brought closer together, the arcuate bands 68 bow outwardly relative to one another. In this manner, the compression member 42 expands in a direction orthogonal to the direction of compression.

The compression member 42 is formed of a substantially elastically deflectable material and has a spring constant (k). In some embodiments, the compression member 42 is formed of PEEK material, although a variety of materials are contemplated, such as polysulfone and shape memory alloys, for example.

As shown in FIGS. 3 and 4, the compression member 42 is secured coaxially with the sleeve 40 by embedding the compression member 42 within the sleeve 40. The compression member 42 is optionally formed within the sleeve 40 as part of a molding operation. For example, the holes 66 (FIG. 5) optionally receive some of the material of the sleeve 40 to help improve coupling of the compression member 42 to the sleeve 40. As assembled, the first and second end portions 60, 62 of the compression member 42 project radially outward from the outer surface 52 of the sleeve 40 (see FIG. 2). In some embodiments, the first and second end portions 60, 62 project out from the outer surface 52 such that they can be grasped by hand or by using a tool to compress the compression member 42. In other embodiments, the end portions 60, 62 are completely embedded within the sleeve 40.

As shown in FIG. 3, the bands 68 extend under the suture grooves 54 of the sleeve 40. In some embodiments, the bands 68 are sufficiently long and/or wide to help reduce force concentrations proximate locations where the sutures 28 are to be tied about the anchoring device 20. For example, the bands 68 assist by distributing compression forces from the sutures 28 (FIG. 1) across a greater portion of the interface at the inner lumen 44 of the anchoring device 20 and the lead 22 (FIG. 2). In some embodiments, the bands 68 are substantially less compliant than the sleeve 40. For example, the compression member 42 is optionally formed of a substantially less compliant material than the sleeve 40 (e.g., PEEK for the compression member 42 and silicone for the sleeve 40).

Some methods of anchoring the lead 22 in the patient's body 12 using the anchoring device 20 include implanting and fixating the lead 22 within the patient's body 12. The anchoring device 20 is axially compressed to increase the effective diameter of at least a portion of the inner lumen 44 to allow the anchoring device 20 to be coaxially slid over the lead 22 to a desired location on the lead 22. In some embodiments, the compression member 42 is compressed by grasping the first and second end portions 60, 62 by hand or using a specialized tool to create a mechanical force advantage for the user.

Figure 6:
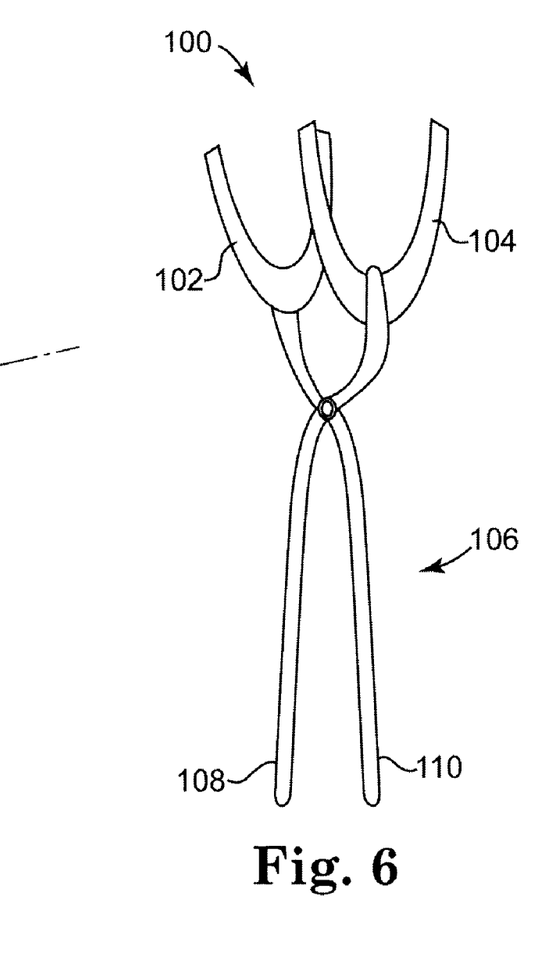
FIG. 6 is an isometric view of a tool for compressing the anchoring device of FIG. 2, according to some embodiments.

For example, FIG. 6 shows a tool 100 for imparting a compressive force to compress the end portions 60, 62. The tool 100 is substantially pliers-like in configuration, the tool 100 having two U-shaped jaws 102, 104 specially adapted for grasping and compressing the protruding end portions 60, 62 and a handle portion 106 including a first handle member 108 connected to the second jaw 104 and a second handle member 110 connected to the first jaw 102. In particular, as the handle of the tool is squeezed, the jaws 102, 104 are closed, thereby compressing the compression member 42. Alternatively, a physician or other user can simply use his or her hands, a forceps, or other means to compress the compression member 42 in some embodiments. Additionally, in some embodiments the tool 100 includes multiple mechanical links or other means to increase mechanical advantage for the user.

As understood with reference to FIGS. 3 and 4, as the compression member 42 is compressed by an external, axial compression force, the effective diameter of the inner bore 50 of the sleeve 40 reversibly increases. In particular, the bands 68 spread apart, which, in turn, forces the inner bore 50 of the sleeve to increase in diameter. In other words, the bands 68 are forced further apart as the end portions 60, 62 are brought closer together. As the bands bow further outward, they force the sleeve 40 outwardly in the transverse direction, thereby increasing the effective diameter of the inner bore 50 at least along the portion of the inner bore 50 generally corresponding to the compression member 42. In different terms, the effective diameter increases in a direction orthogonal to the direction of applied compression. This expansion reverses, i.e., the effective diameter decreases, upon removal of the compressive force.

Once the anchoring device 20 is positioned along the lead 22 (FIG. 1) as desired, the compression member 42 is released, or the external compression force is otherwise removed. Upon removal of the external, axial compression force, the compression member 42 returns to its natural state at a predetermined equilibrium to apply a desired compressive force on the lead 22. As the compression member 42 transitions to this natural state, the inner lumen 44 of the anchoring device 20, and in particular the inner bore 50 of the sleeve 40, reduces in effective diameter to begin compressively engaging the lead 22 or, if already engaging the lead 22, to begin engaging the lead 22 to a greater extent, thereby exerting an increased retaining force on the lead 22. In some embodiments, the raised portion 53 helps increase the retaining force on the lead 22 without the compression force being sufficiently concentrated to cause lead damage.

The sutures 28 (FIG. 1) are aligned to the suture grooves 54 and tightened about the anchoring device 20 to secure the anchoring device 20 to surrounding tissue of the patient's body 12 (FIG. 1). Although in some embodiments the compression member 42 can supply sufficient retaining force alone, the sutures 28 can also help further secure the anchoring device 20 to the lead 22 by applying additional compressive forces onto the lead 22. For example, as the sutures 28 are tightened, the anchoring device 20 is further compressed onto the lead 22, although the less compliant compression member 42 helps to limit, or otherwise inhibit local force concentrations from the sutures 28. Additionally, if the sutures 28 begin to cut through the anchoring device 20, the less compliant compression member 42 can help prevent cutting of the sutures 28 through the anchoring device 20 and into the lead 22.

In some embodiments, the compression member 42 is adapted to be compressible up to a pre-selected amount to limit the maximum compressive forces exerted on the lead 22 by the anchoring device 20. For example, if the compression member 42 is sufficiently compressed such that the gaps 70 between adjacent bands 68 are closed, the bands 68 either directly abut against one another or indirectly abut through adjacent material (e.g., portions of the sleeve 40 residing in the gaps 70) to resist further compression of the anchoring device 20. In some embodiments, the physician is provided tactile feedback that the anchoring device 20 is in the closed state or has reached the limit and ceases tightening the sutures 28 once the gaps 70 are closed or otherwise sufficiently resist further tightening.

Figure 7:
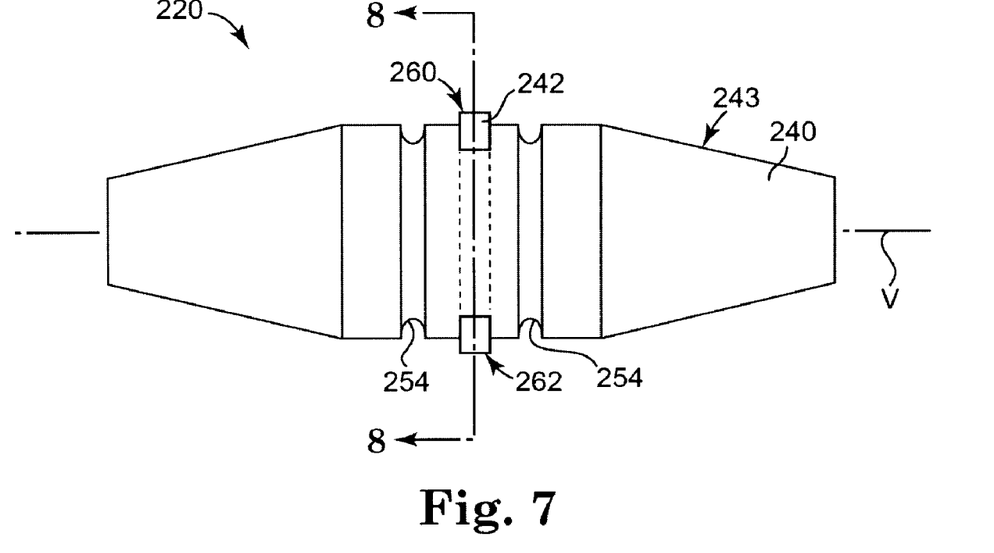
FIG. 7 is a front view of another anchoring device of the anchoring system of FIG. 1, according to some embodiments.
Figure 8:
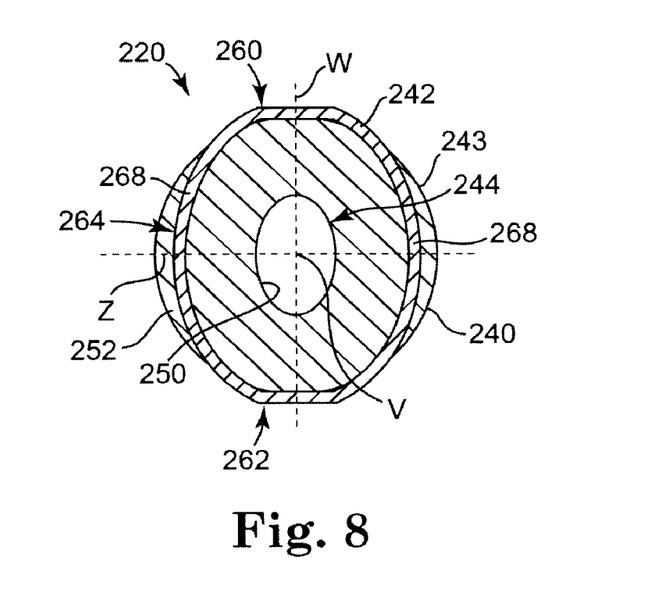
FIG. 8 is a transverse cross-section of the anchoring device of FIG. 6 taken along line 8-8 of FIG. 7.

FIGS. 7 and 8 show another anchoring device 220 suitable for use in the system 10. For example, the anchoring device 220 is optionally used in a substantially similar manner, according to substantially similar methods, to the anchoring device 20 to secure the lead 22 within the patient's body 12.

FIG. 7 is a front view of the anchoring device 220 and FIG. 8 is a transverse cross-section of the anchoring device 220 taken along line 8-8 of FIG. 7. As shown in FIGS. 7 and 8, the anchoring device 220 includes a sleeve 240 and a compression member 242. Overall, the anchoring device 220 has an outer surface 243, an inner lumen 244 (FIG. 8) adapted to receive the lead 22, and is substantially elongate, tubular, and tapered toward each end of the anchoring device 220.

In some embodiments, the sleeve 240 generally defines the substantially elongate, hollow, tubular, and tapered shape of the anchoring device 220. The sleeve 240 defines an inner bore 250 (FIG. 8) and an outer surface 252. According to some embodiments, the sleeve 240 is formed of an elastomeric material and is generally flexible, substantially compliant, and elastically compressible. For example, the sleeve 240 is formed of silicone or other materials having suitable properties, including those previously described.

The outer surface 252 of the sleeve 240 has a plurality of circumferentially extending suture grooves 254 (FIG. 7) formed into the outer surface 252. The sleeve 240 also optionally includes features such as longitudinal slots (not shown) for facilitating compression of the sleeve 240. The inner bore 250 has a substantially oval-shaped transverse cross-section defining a major axis along axis W and a minor axis along axis Z shown in FIG. 8. As previously referenced, the effective diameter of the inner bore 250 corresponds to the minor axis of the oval shape.

As shown in FIG. 8, the effective diameter of the inner bore 250 is substantially constant. In particular, the inner bore 250 is substantially smooth. In other embodiments, the inner bore 250 has a taper (not shown), a centrally-located and circumferentially-extending raised portion (not shown), or other means for enhancing frictional enhancement between the lead 22 and the anchoring device 220.

As shown in FIGS. 7 and 8, the compression member 242 defines a central longitudinal axis V and includes a first end portion 260, a second end portion 262, and an intermediate portion 264 extending between the first and second end portions 260, 262. Each of the first and second end portions 260, 262 is formed as a flat band, although other shapes are contemplated. The compression member 242 is formed of a substantially elastically deflectable material and defines a spring constant (k). In some embodiments, the compression member 242 is formed of PEEK material, polysulfone, or shape-memory alloys, although a variety of materials are contemplated, such as those previously described.

The intermediate portion 264 is formed of a plurality of arcuate bands 268, two as shown in FIG. 7. The arcuate bands 268 are disposed on opposite sides of the central longitudinal axis V. As shown, each of the bands 268 is curved in a transverse plane of the compression member 242.

The bands 268 are adapted to elastically reversibly deform outward relative to the central longitudinal axis V upon compression of the first and second end portions 260, 262 along the axis W. In particular, as the two end portions 260, 262 are brought closer together, the arcuate bands 268 bow outwardly relative to one another. In this manner, the compression member 242 expands along axis Z in a direction orthogonal to the direction of compression, the direction of compression being along axis W of FIG. 8. Once a compressive force causing the deformation has been removed, the end portions 260, 262 and bands 268 substantially return to their natural position at a force equilibrium with the lead 22 when coaxially disposed within the anchoring device 220.

As shown in the figures, the compression member 242 is secured coaxially with the sleeve 240 by embedding at least a portion of the compression member 242 (e.g., the bands 268) within the sleeve 240. For example, the compression member 242 is optionally formed within the sleeve 240 as part of a molding operation. As assembled, the first and second end portions 260, 262 of the compression member 242 project radially outward from the outer surface 252 of the sleeve 240.

Figure 9:
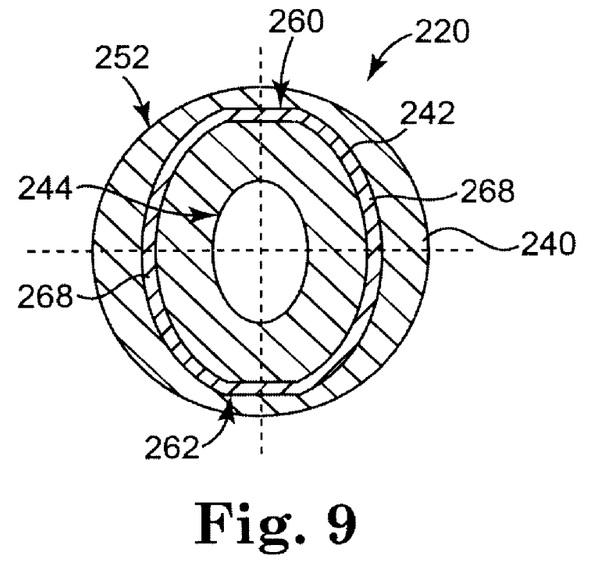
FIG. 9 is a cross-sectional view showing another anchoring device configuration according to some other embodiments.
Figure 10:
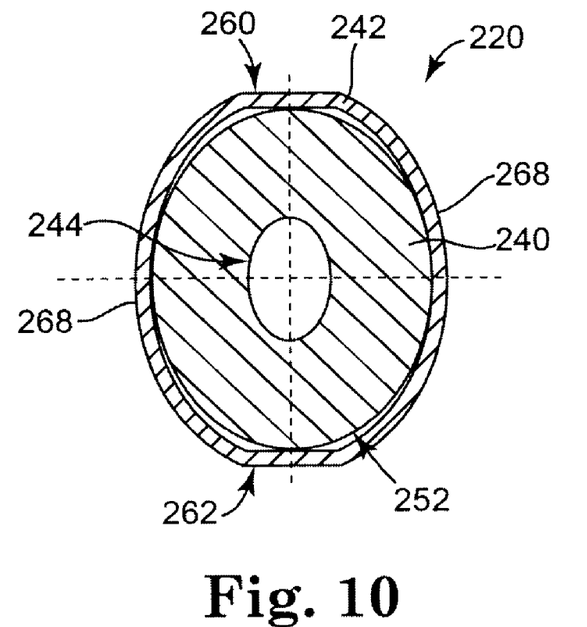
FIG. 10 is a cross-sectional view showing yet another anchoring device configuration according to still other embodiments.

In some embodiments, the first and second end portions 260, 262 project from the outer surface 252 such that they can be grasped by hand or using a tool (e.g., a forceps) to compress the compression member 242 (see FIG. 7). FIG. 9 is a cross-sectional view showing another configuration of the anchoring device 220. As shown in FIG. 9, in other embodiments, the end portions 260, 262 are completely embedded within the sleeve 240. FIG. 9 is a cross-sectional view showing yet another configuration of the anchoring device 220. As shown in FIG. 10, in still other embodiments, the compression member 242 is secured to the outer surface 252 of the sleeve 240.

In still other embodiments (not shown), the bands 268 extend under the suture grooves 254 of the sleeve 240 and are sufficiently wide to help reduce force concentrations proximate locations where the sutures 28 are to be tied about the anchoring device 220. For example, the bands 268 can assist by distributing compression forces from the sutures 28 across a greater portion of the interface at the inner lumen 244 of the anchoring device 220 and the lead 22 as previously referenced.

As understood with reference to FIGS. 7 and 8, as with various other embodiments, some methods of anchoring the lead 22 (FIG. 1) in the patient's body 12 (FIG. 1) using the anchoring device 220 include implanting and fixating the lead 22 within the patient's body 12. The anchoring device 220 is axially compressed along its major axis to increase the effective diameter of at least a portion of the inner lumen 244 to allow the anchoring device 220 to be coaxially slid over the lead 22 to a desired location on the lead 22. In some embodiments, the compression member 242 is compressed by grasping the first and second end portions 260, 262 by hand or using a forceps (not shown) or other appropriate tool.

Once the compression member 242 is released, it returns to a natural state to compress the sleeve inner bore 250 against the lead 20, thereby retaining the anchoring device 220 on the lead 22. The sutures 28 (FIG. 1) are then used to secure the anchoring device 220 to surrounding tissue and/or to further compress the anchoring device 220 onto the lead 22.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An implantable medical system comprising:
   a medical lead including an insulating sheath and a conductor; and
   an anchoring device defining an inner lumen adapted to coaxially receive the medical lead, the inner lumen having an effective diameter, the anchoring device including:
   a sleeve including a substantially elongate, elastomeric body defining an outer surface, the inner lumen extending through the sleeve; and
   a compression member including a first end, a second end, and an intermediate portion between the first and second ends, the compression member being at least partially embedded in the sleeve such that compression of the first and second ends of the compression member toward one another causes the effective diameter of at least a portion of the inner lumen extending through the sleeve of the anchoring device to reversibly increase in order to permit the anchoring device to slide relative to the lead, wherein the compression member includes a first collar, a second collar, and a plurality of substantially arcuate bands extending between the first and second collars, and each of the first and second collars project radially outward from the outer surface of the sleeve.

2. The system of claim 1, wherein the compression member defines a central longitudinal axis and the sleeve defines a central longitudinal axis and further wherein the compression member is coaxial with the sleeve along the longitudinal axes of the compression member and the sleeve, respectively.

3. The system of claim 1, wherein each of the plurality of substantially arcuate bands is embedded in the elastomeric body of the sleeve.

4. The system of claim 1, wherein the compression member is formed of PEEK.

5. The system of claim 1, wherein the compression member includes a substantially continuous ring defining a major axis and a minor axis shorter than the major axis such that upon compression of the compression member along the major axis the effective diameter of the inner lumen reversibly increases in the direction of the minor axis.

6. An anchoring device for anchoring a medical lead implanted in a patient, the anchoring device comprising:
   a sleeve defining a central longitudinal axis and including a substantially elongate, hollow, tubular, and elastomeric body defining an outer surface and an inner bore having an effective diameter, the inner bore extending through the sleeve; and
   a compression member defining a central longitudinal axis coaxially aligned with the central longitudinal axis of the sleeve, the compression member including first and second opposing portions exposed from the outer surface of the sleeve and an intermediate portion extending between the first and second portions and defining a second diameter, the compression member adapted such that upon compression of the first and second opposing portions toward one another the second diameter reversibly increases which causes the effective diameter of the inner bore extending through the sleeve to reversibly increase, wherein the compression member includes a first collar, a second collar, and a plurality of substantially arcuate bands extending between the first and second collars, and each of the first and second collars project radially outward from the outer surface of the sleeve.

7. The anchoring device of claim 6, wherein each of the plurality of substantially arcuate bands is at least partially embedded in the elastomeric body of the sleeve.

8. The anchoring device of claim 6, wherein the compression member includes a substantially continuous ring defining a major axis and a minor axis shorter than the major axis such that upon compression of the compression member along the major axis the effective diameter of the inner bore reversibly increases, and further wherein the first and second portions of the compression member are positioned opposingly along the major axis.

9. An anchoring device for anchoring a medical lead implanted in a patient, the anchoring device comprising:
   a sleeve including a substantially elongate, elastomeric body defining an outer surface and an inner bore extending through the sleeve, the inner bore having a diameter; and
   a compression means for causing the diameter of the inner bore extending through the sleeve to reversibly increase in a direction orthogonal to a major axis of the sleeve, the compression means being at least partially embedded in the sleeve, wherein the compression means includes a first collar, a second collar, and a plurality of substantially arcuate bands extending between and connected to the first collar and the second collar, and each of the first and second collars project radially outward from the outer surface of the sleeve.

10. The anchoring device of claim 9, wherein the compression means includes a compression member defining a central longitudinal axis, wherein the sleeve defines a central longitudinal axis, and further wherein the compression means is coaxial with the sleeve along the central longitudinal axes of the compression member and the sleeve, respectively.

11. The anchoring device of claim 9, wherein each of the plurality of substantially arcuate bands is embedded in the elastomeric body of the sleeve.

12. The anchoring device of claim 9, wherein the compression means includes a substantially continuous ring defining a major axis and a minor axis that is shorter than the major axis, and further wherein the anchoring device is configured such that compression of the compression member along the major axis reversibly increases the diameter of the inner bore of the sleeve in a direction of the minor axis.

13. The anchoring device of claim 9, wherein the sleeve is formed of a material including silicone.

14. The anchoring device of claim 9, wherein the compression means is adapted to be compressible up to a pre-selected minimum transverse cross-sectional area in order to limit compressive forces exerted on the lead by the anchoring device.

* * * * *